(12) United States Patent
Löhn

(10) Patent No.: US 8,839,685 B2
(45) Date of Patent: Sep. 23, 2014

(54) SYRINGE FOR USE WITH A DOSING DEVICE

(75) Inventor: Jürgen Löhn, Gross Meckelsen (DE)

(73) Assignee: Eppendorf AG, Hamburg (DE)

( * ) Notice: Subject to any disclaimer, the term of this patent is extended or adjusted under 35 U.S.C. 154(b) by 160 days.

(21) Appl. No.: 13/211,886

(22) Filed: Aug. 17, 2011

(65) Prior Publication Data

US 2012/0204660 A1 Aug. 16, 2012

Related U.S. Application Data

(60) Provisional application No. 61/411,114, filed on Nov. 8, 2010.

(30) Foreign Application Priority Data

Aug. 30, 2010 (DE) .......................... 10 2010 035 891

(51) Int. Cl.
*G01N 1/14* (2006.01)
*B01L 3/02* (2006.01)
*A61M 5/315* (2006.01)

(52) U.S. Cl.
CPC ....... *B01L 3/0234* (2013.01); *B01L 2200/0605* (2013.01); *A61M 2005/31816* (2013.01); *B01L 2300/0851* (2013.01); *A61M 5/31573* (2013.01); *A61M 5/31513* (2013.01)
USPC ...................... 73/864.13; 73/864.16; 422/501

(58) Field of Classification Search
USPC .......... 73/864.16, 864.13; 422/501, 516, 521, 422/522
See application file for complete search history.

(56) References Cited

U.S. PATENT DOCUMENTS

| 4,406,170 | A | | 9/1983 | Kuhn |
| 4,468,223 | A | * | 8/1984 | Minagawa et al. ........... 604/199 |
| 4,483,825 | A | * | 11/1984 | Fatches ........................ 422/513 |
| 5,591,408 | A | | 1/1997 | Belgardt et al. |
| 5,620,660 | A | | 4/1997 | Belgardt et al. |

(Continued)

FOREIGN PATENT DOCUMENTS

| DE | 12 25 819 | 9/1966 |
| DE | 29 26 691 C2 | 5/1981 |

(Continued)

OTHER PUBLICATIONS

Company publication of: Ritter Medical Care: ritips., Schwabmunchen, 24.09*.2008.

*Primary Examiner* — Peter Macchiarolo
*Assistant Examiner* — Natalie Huls
(74) *Attorney, Agent, or Firm* — Vidas, Arrett & Steinkraus, P.A.

(57) ABSTRACT

A syringe for use with a dosing device with a receiver for a syringe cylinder and an axially displaceable plunger receiver for a syringe plunger with
a syringe cylinder,
which has a floor with an outlet on the bottom,
a cylindrical plunger run area on the inside and
has means for being held in the receiver on the top,
a syringe plunger,
which has a circumferential plunger seal for sealing on the plunger run area on the perimeter and
a coupling piece for insertion into the plunger receiver on the top and
stop means between the syringe cylinder and the syringe plunger, which restrict the displacement of the syringe plunger towards the floor so that the syringe plunger with the plunger seal can only approach to a certain distance from the floor.

16 Claims, 12 Drawing Sheets

(56) References Cited

U.S. PATENT DOCUMENTS

| | | | |
|---|---|---|---|
| 5,704,918 A * | 1/1998 | Higashikawa | 604/191 |
| 7,198,619 B2 * | 4/2007 | Bills et al. | 604/218 |
| 2003/0212372 A1 | 11/2003 | Bills et al. | |
| 2005/0063857 A1 * | 3/2005 | Alheidt et al. | 422/28 |
| 2006/0263261 A1 | 11/2006 | Lenz | |
| 2007/0169571 A1 * | 7/2007 | May et al. | 73/864.13 |
| 2007/0293822 A1 * | 12/2007 | Crawford et al. | 604/175 |
| 2009/0004063 A1 * | 1/2009 | Higashihara et al. | 422/99 |
| 2009/0216188 A1 * | 8/2009 | Woehr et al. | 604/110 |

FOREIGN PATENT DOCUMENTS

| | | |
|---|---|---|
| DE | 43 41 229 C2 | 9/1995 |
| DE | 690 22 066 T2 | 2/1996 |
| DE | 692 32 513 T2 | 11/2002 |
| DE | 697 33 769 T2 | 1/2006 |
| DE | 601 12 561 T2 | 2/2006 |
| DE | 10 2005 023 203 A1 | 11/2006 |
| DE | 10 2009 034 897 A1 | 2/2011 |
| EP | 0 679 439 B1 | 11/1995 |

\* cited by examiner

Figure 1:
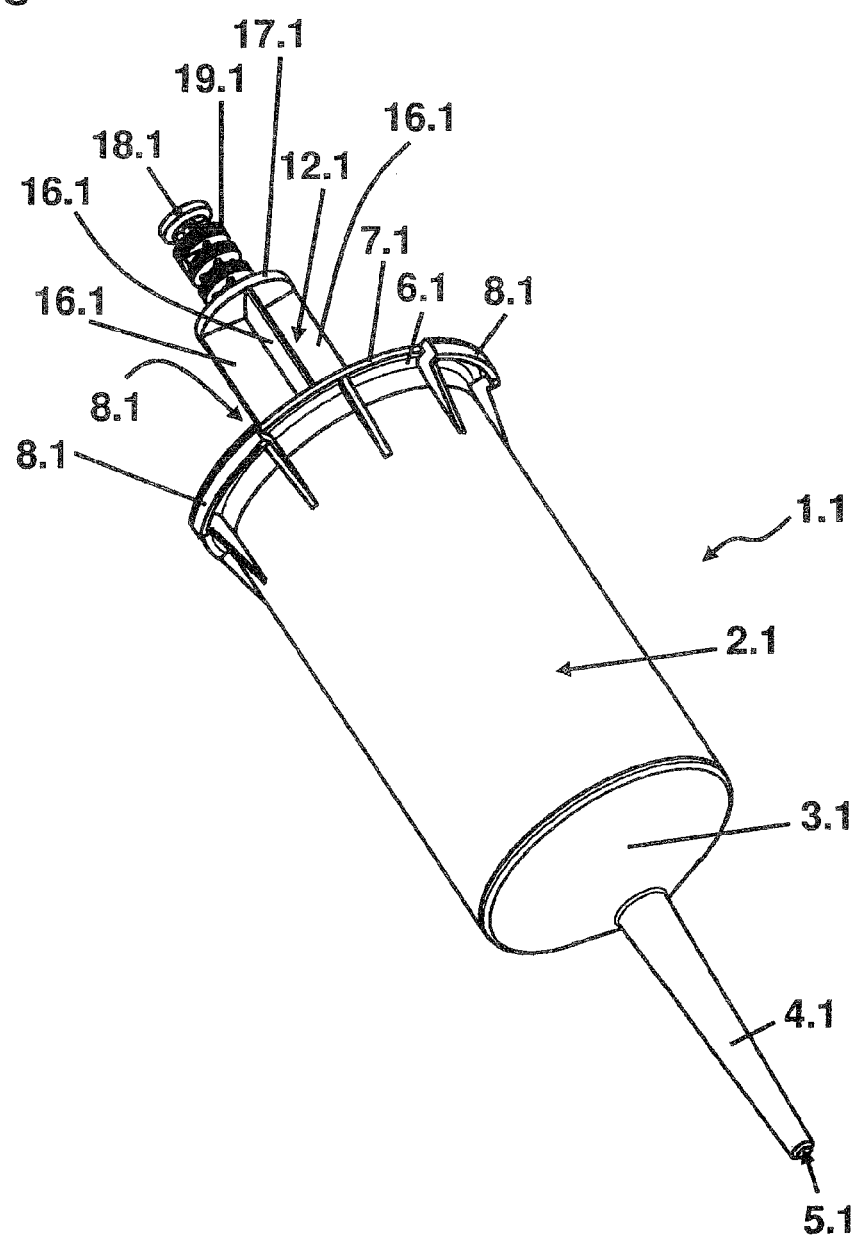

Fig. 1    "PRIOR ART"

Fig. 2 "PRIOR ART"

"PRIOR ART"

SYRINGE FOR USE WITH A DOSING DEVICE

The invention relates to a syringe with a syringe cylinder and syringe plunger for use with a dosing device, which has a receiver for the syringe plunger and an axially displaceable plunger receiver for the syringe plunger.

Pipettes are dosing devices for measuring and transferring liquids. They are often designed as repetition pipettes or multipettes, which are used together with a syringe, in order to receive liquid into the syringe and to dispense it from there incrementally. A repetition pipette is known from DE 29 26 691 C2 and U.S. Pat. No. 4,406,170. In this case, the syringe receiver is a U-shaped groove in a pipette housing, into which a syringe flange can be inserted through a lateral housing opening. In the receiver, the syringe flange is loaded by a pressure spring in the direction of the dispensing opening. The syringe plunger has a cylindrical actuation section, which can be secured in a receiving body by means of a clamping device.

A plunger push back device is designed as a lever of the receiving body, which protrudes through a lateral housing slit. By moving the lever of the syringe flange away, the plunger can be pulled out of the syringe. The plunger advancing device is a shaft ratchet device wherein the shaft is connected with the receiving body and the ratchet is swivel mounted on a drive lever that can be moved back and forth. When pivoting the drive lever towards the syringe flange, the ratchet locks in place and takes along the shaft and the connected plunger in the same direction. When pivoting in the opposite direction, the ratchet jumps out of the serrated toothing and the plunger position doesn't change. An incremental setting device has a tongue coupled with a rotary knob, which more or less covers the toothing depending on the position of the rotary knob. By setting the rotary knob, the section of the ratchet movement is adjustable, in that they engage in the shaft and take the plunger along. Thus, the liquid volume dispensed from the syringe in each dosing step can be adjusted by means of the rotary knob.

The syringe sits in its receivers with a certain play. Moreover, the pusher devices have play. As a result, the plunger is moved a different distance than in the subsequent steps after being pulled out at a constant increment setting. The liquid amount discharged in the first step thus deviates considerably from the liquid discharge of each subsequent step. Thus, for an exact dosing, the liquid volume discharged in the first step is discarded in practice. Sample liquid is hereby lost.

EP 0 679 439 B1 and U.S. Pat. No. 5,591,408 describe a further developed repetition pipette, which has a constant step device for the reduction of the loss of sample liquid, which determines the size of the extent of the discharge step for a constant value regardless of the setting of the setting element for further subsequent steps.

DE 43 41 229 C2 and U.S. Pat. No. 5,620,660 suggest a pipette system better suited for manual actuation with a syringe easily axially insertable or respectively removable pipette. This pipette system has a syringe with a fastening section and a syringe plunger and a pipette, which in a pipette housing has a receiver for the fastening section and a receiver body with a plunger receiver for the syringe plunger or respectively a plunger rod connected with it. Furthermore, fastening devices for reversible or respectively releasable securing of fastening section and syringe plunger in the receivers and plunger setting devices for adjusting the receiver body in the pipette housing are present. The fastening section and the syringe plunger are axially pushable into their fastening positions through axial openings in their receivers.

The fastening devices have radially advancible grip devices for fixing the fastening section and the syringe plunger in the fastening positions. The grip devices have syringe grip levers swivel mounted in the pipette housing and plunger grip levers swivel mounted in the receiver body. The syringe grip levers and the plunger grip levers are designed with two arms with a grip arm and an actuation arm, wherein the syringe grip levers have contact points on the insides of their actuation arms, which are pivotable by actuating their actuation arms on the outside against the actuation arms of the plunger grip lever and actuate the plunger grip levers.

It is hereby achieved that the syringe and the pipette are interconnectable through a purely axial relative movement and are separable from each other through actuation of the actuation arms. According to one embodiment, the fastening section is a syringe flange and, according to another embodiment, the syringe plunger has a plunger collar for engaging behind through the grip devices.

An embodiment of the pipette according to DE 43 41 229 C2, in which the syringe is releasable from the pipette through actuation of just one single actuator, is known from DE 10 2005 023 203 and US 2006263261 A1.

The commercial embodiments Multipette® (plus/stream/Xstream) of this dosing system made by Eppendorf AG comprise syringes Combitips® (plus), which have a cylinder with a plunger run area on the inside and a syringe flange on the upper end of the cylinder. The syringes are offered with different fill volumes (0.1 ml, 0.2 ml, 0.5 ml, 1 ml, 2.5 ml, 5 ml and 10 ml). Furthermore, the system comprises syringes Combitips® (plus) with volumes of 25 ml and 50 ml. These syringes have a large cross-section and are connectable with a repetition pipette via an adapter. The adapter is connected with the upper edge of the syringe cylinder on a large diameter via a bayonet joint. On the top, it has a sleeve with a smaller diameter with a flange according to the syringe flange of the smaller syringes. The adapter is connected with the repetition pipette via the syringe flange.

The known dosing system enables exact dosing with small measurement deviations.

Based on this, the object of the invention is to provide a syringe for use with a dosing device, which enables even more exact dosings.

The object is solved through a syringe with the characteristics of claim 1.

The syringe according to the invention for use with a dosing device with a receiver for a syringe cylinder and an axially displaceable plunger receiver for a syringe plunger has
a syringe cylinder,
which has a floor with an outlet on the bottom,
a cylindrical plunger run area on the inside and
has means for being held in the receiver on the top,
a syringe plunger,
which has a circumferential plunger seal for sealing on the plunger run area on the perimeter and
a coupling piece for insertion into the plunger receiver on the top and
stop means between the syringe cylinder and the syringe plunger, which restrict the displacement of the syringe plunger towards the floor so that the syringe plunger with the plunger seal can only approach to a certain distance from the floor.

The invention is based on the surprising realization by the applicant that, in the case of the incremental discharge of sample liquid, a somewhat larger liquid amount is discharged during the last dosing step than during the previous discharge steps. Furthermore, comprehensive examinations by the applicant have led to the surprising result that this increased liquid discharge is due to the fact that, during the last dosing step, the floor of the syringe cylinder is deformed by a very small amount towards the inside of the syringe cylinder. The applicant found that this is attributed to the radial broadening of the syringe cylinder by the sealing lip of the syringe plunger approaching the floor. As a result, a general displacement of liquid by the shifting of the syringe plunger occurs in addition to an unintentional additional displacement of liquid through the shifting of the floor. The syringe according to the invention overcomes this effect in that it has stop means, which restrict the displacement of the syringe plunger to the floor so that the syringe plunger with the plunger seal can only approach to a certain distance from the floor. The distance is selected such that the deformation of the floor is reduced or avoided, which in the case of the approaching of the plunger seal leads to an increased discharge of liquid. It is preferably 1 mm or more. The dosing accuracy of the last discharge step is hereby improved and better matches the dosing accuracy of the previous dosing steps.

According to one embodiment, the syringe plunger below the plunger seal has a bottom plunger section, which engages in a bottom end area of the syringe cylinder once the plunger seal has approached to a certain distance from the floor. The bottom plunger section mainly fills the volume in the syringe cylinder below the plunger seal. Air pockets between syringe plunger and liquid taken into the syringe, which can impair the dosing accuracy, are hereby mainly avoided. The lower plunger section is preferably dimensioned such that the air pockets occur as infrequently as possible, but the flow resistance in the created gap during the discharge of the remainder remains in the acceptable range, in which the force for to be used for the discharge of the remainder is not too large from a subjective point of view. For this, the extent of the gap between the lower plunger section and the lower end area of the syringe cylinder is preferably a few tenths of a millimeter.

The stop means between the syringe cylinder and the syringe plunger can be designed differently. According to one embodiment, the stop means have a circumferential inner step of the syringe cylinder, which is arranged at a distance from the floor and restricts the displacement of the syringe plunger towards the floor. The displacement of the syringe plunger is thereby preferably restricted in that the sealing lip rests on the inner step of the syringe cylinder. When the syringe plunger rests on the inner step, the plunger seal is located at a distance from the floor such that the radial broadening of the syringe cylinder in the area of the plunger seal in the area of the plunger seal results in no or considerably reduced deformation (compared to conventional syringes) of the floor towards the inside, which noticeably impairs the dosing accuracy of the last dosing step.

A syringe cylinder with an inner step has a lower end area with a preferably reduced inner diameter below the inner step. This is due to the production of the syringe cylinder through injection molding. The syringe plunger preferably engages in this lower end area with a lower plunger section with a reduced diameter when the syringe plunger is inserted as far as possible into the syringe cylinder.

According to one embodiment, the syringe cylinder has at least adjacent to the floor ribs extending axially around its perimeter on the outside. The axial ribs counteract a radial expanding of the syringe cylinder during insertion of the syringe plunger and an inwards deformation of the floor into the syringe cylinder. The dosing error is hereby further reduced. According to another embodiment, the syringe cylinder in the lower end area with the reduced diameter has axially extending ribs on the outside. The axial ribs should preferably be measured such that they lie within the intended elongation of the casing of the syringe cylinder in the plunger run area. The ribs do not then protrude over the casing of the syringe cylinder in the plunger area towards the outside. According to a further embodiment, the axial ribs are evenly distributed over the perimeter of the syringe cylinder.

Furthermore, the object is solved through a syringe with the characteristics of claim 7.

The syringe according to the invention for use with a dosing device with a receiver for a syringe cylinder and an axially displaceable plunger receiver for a syringe plunger has
    a syringe cylinder,
        which has a floor with an outlet on the bottom,
        on the outside of the floor radially extending ribs with a height of at least 1 mm at least on the outer end,
        a cylindrical plunger run area on the inside and
        has means for being held in the receiver on the top and
    a syringe plunger,
        which has a circumferential plunger seal for sealing on the plunger run area on the perimeter and
        a coupling piece for insertion into the plunger receiver on the top.

In the case of the syringe according to the invention, a deformation of the floor into the syringe cylinder is counteracted during the last dosing step in that the floor is reinforced by radially extending ribs. A displacement of liquid through deformation of the floor is hereby avoided in addition to a displacement of liquid through shifting of the syringe plunger. The dosing accuracy of the last dosing step is also improved in this syringe.

Syringes ritips® professional e.g. 10 ml, which have eight radially extending ribs on the floor, are known from the market. However, these radially extending ribs have a maximum height of less than one millimeter at the outlet of the floor and their height decreases radially outward to a value of zero on the outer perimeter of the floor. These ribs are apparently applied for aesthetic reasons. Due to their measurement and their progression, the radially extending ribs are not suitable for reducing the inward deformation of the floor into the syringe cylinder during the last discharge step.

According to a preferred embodiment, a syringe according to claim 1 or related dependent claim has the characteristics of claim 7.

According to another embodiment, the ribs have at least on the outer end a height of at least 3 mm, more preferably of at least 5 mm. In the case of this embodiment, an inward deformation of the floor into the syringe cylinder during the last dosing step is further reduced.

The invention includes embodiments, in which the radial ribs have a constant height or the height of the radial ribs increases towards the outlet from the floor. According to one embodiment, the height of the radial ribs decreases towards the outlet. It can hereby be avoided that the ribs interfere during the receiving and discharging of sample liquids. According to another embodiment, the radial ribs are evenly distributed over the floor in the circumferential direction.

According to another embodiment, the syringe cylinder has a cylindrical elongation overlapping the floor laterally and the radial ribs extend from the inside of this elongation radially towards the inside. The floor is hereby further reinforced.

According to another embodiment, that applies to all invention variants, the outlet is arranged in a dosing tip protruding from the floor on the outside. The radial ribs preferably run flat towards the dosing tip.

According to another embodiment, the syringe plunger has a displacement tip on the bottom, which engages into the dosing tip when the syringe plunger is pushed as far as possible into the syringe cylinder. There is then preferably a small gap between displacement tip and dosing tip. This counteracts an air cushion between the syringe plunger and the taken in liquid.

According to another embodiment, the floor has a downward tapering, conical shape. This shape in combination with radial ribs, the height of which decreases towards the outlet, prevents the radial ribs from interfering during the receiving and dispensing of liquid.

According to another embodiment, the syringe plunger has a plunger head, which is connected with a coupling piece via a push rod. A material-saving design of the syringe plunger is hereby achieved. According to another embodiment, the push rod has several wing pieces extending in the longitudinal direction. The wing pieces promote a stable push rod with low material use.

According to another embodiment, the means for holding a flange connected as one piece with the syringe cylinder and/or an adapter connected with the syringe cylinder with a flange and/or means for connecting the syringe cylinder with an adapter. The adapter is preferably connected with the syringe cylinder through a bayonet joint or screw connection.

According to another embodiment, the plunger seal is a sealing lip on the perimeter of the syringe plunger. According to another embodiment, the sealing lip is a collar oriented at an acute angle towards the perimeter of the syringe plunger. According to another embodiment, the sealing lip is pointed towards the floor.

The syringe according to the invention is preferably produced with fill volumes of 10 ml, 12.5 ml, 25 ml and 50 ml. The dosing error during the last dosing step is brought to bear especially in conventional syringes with the named fill volumes.

According to one embodiment, the syringe cylinder and/or the syringe plunger are each made of a single piece of plastic.

In this application, the specifications "on the top" or "on the bottom" refer to the preferred arrangement of the syringe during dosing, in which the syringe is held perpendicular with the outlet on the bottom and the coupling piece on the top.

Figure 2:
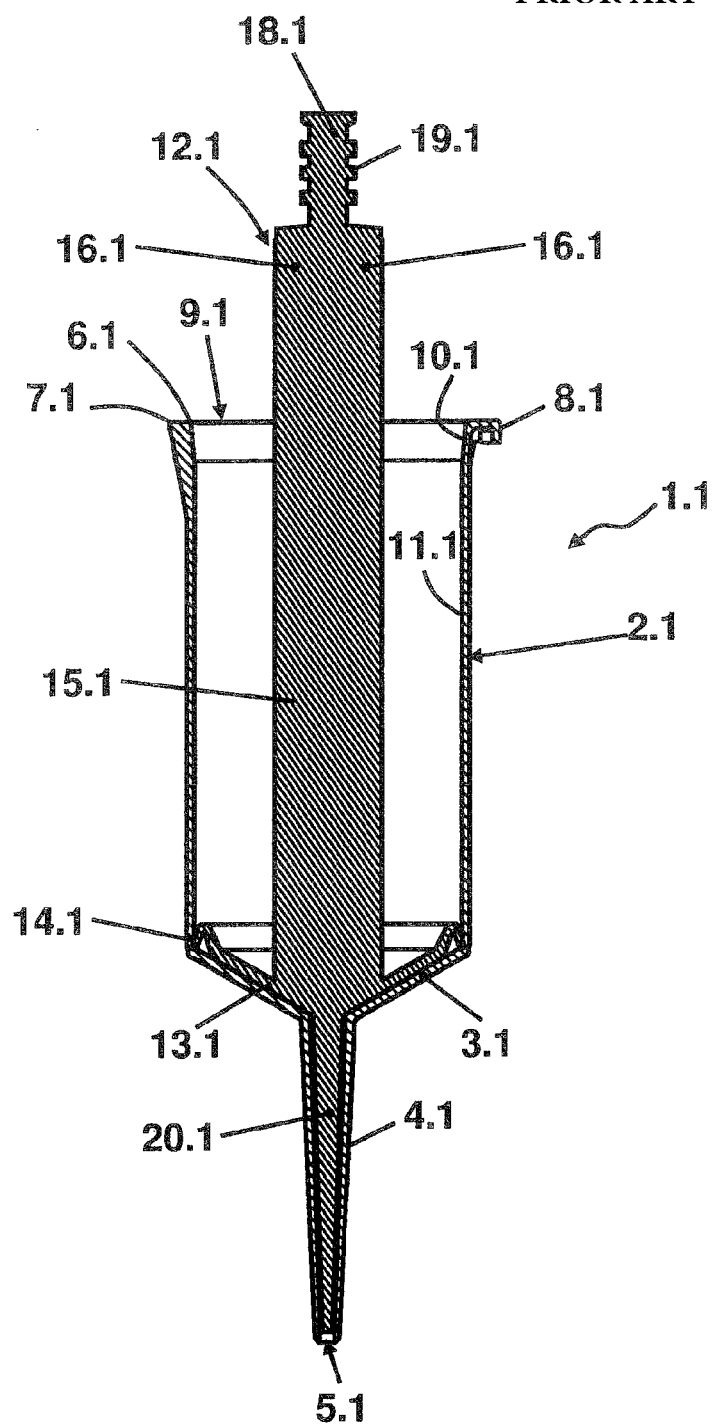
Figure 3:
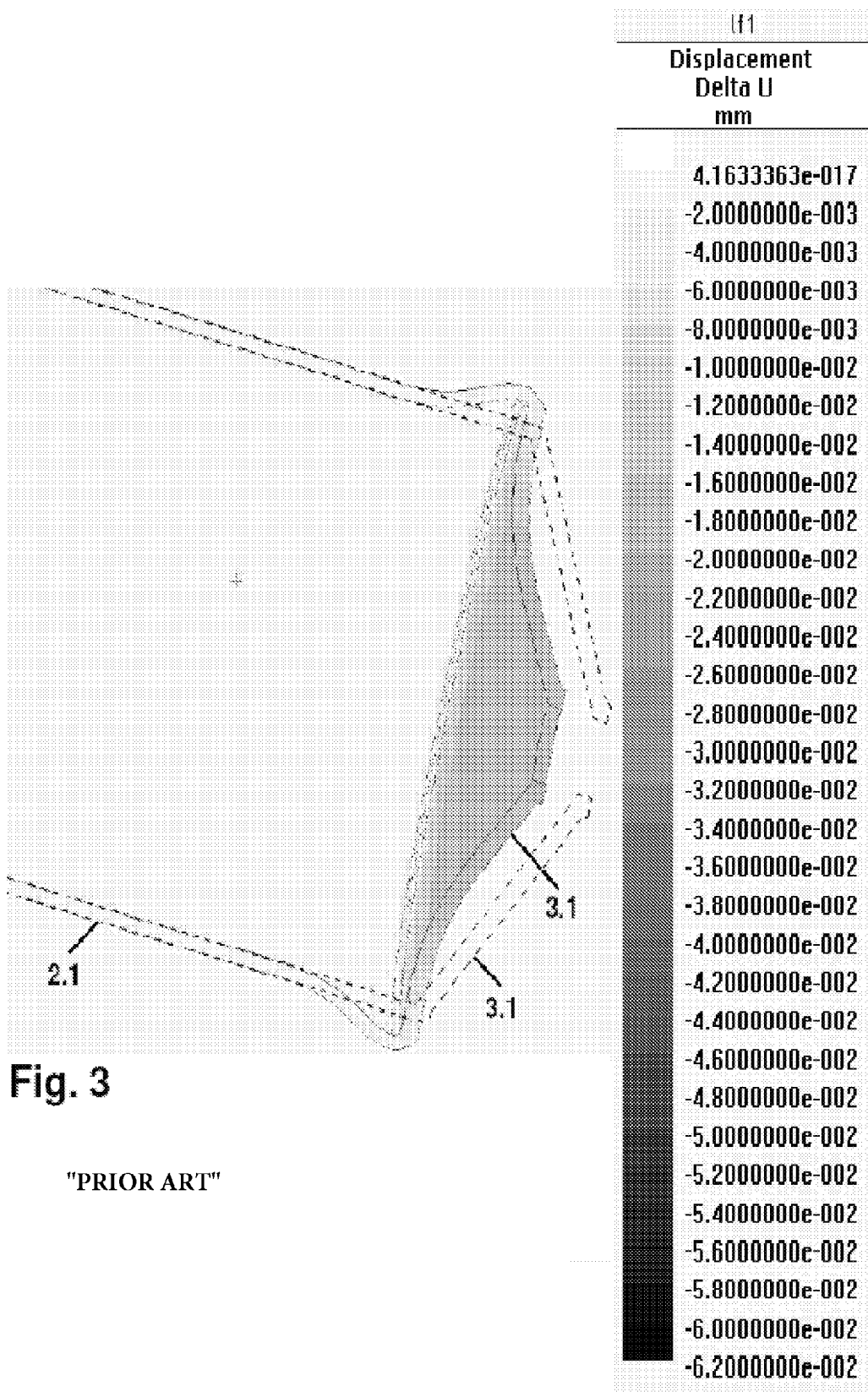
Figure 4:
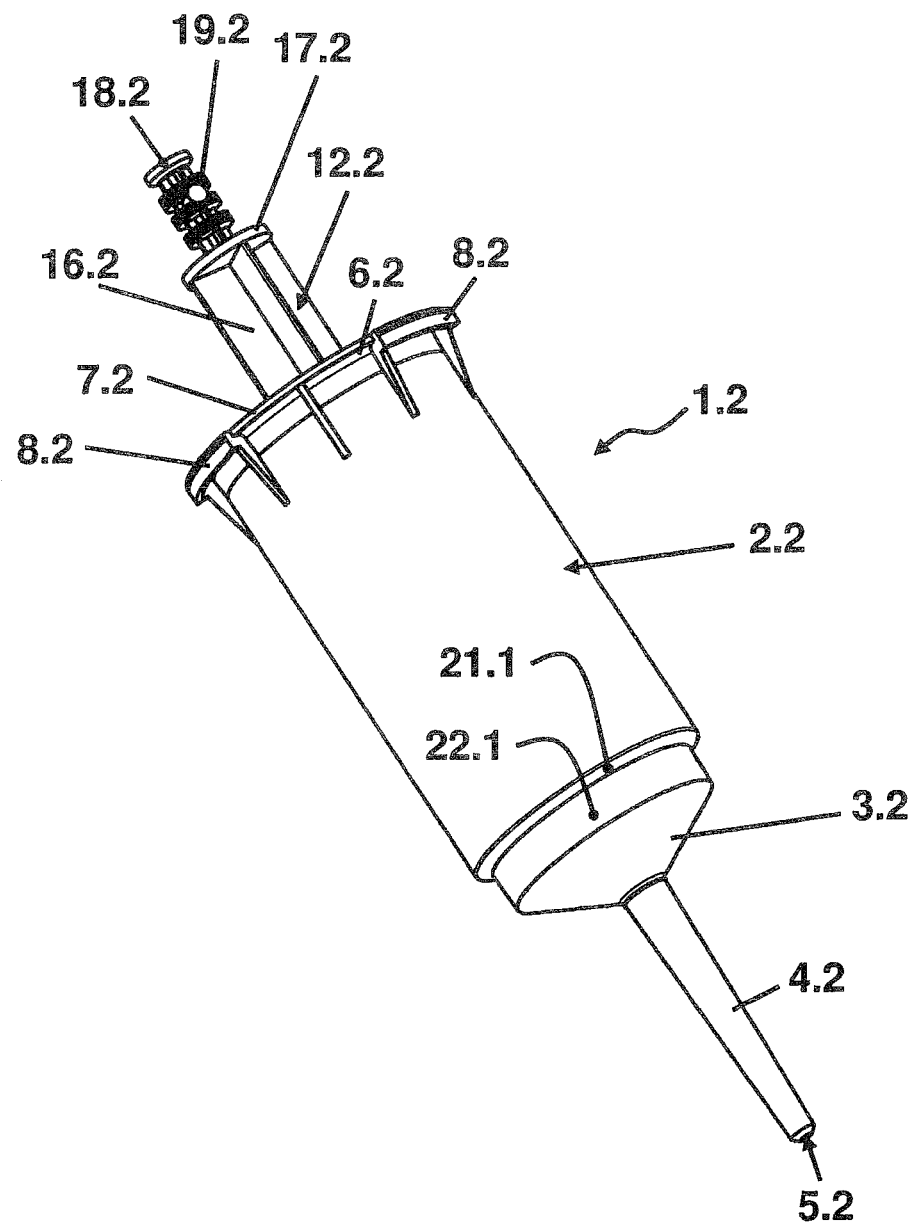
Figure 5:
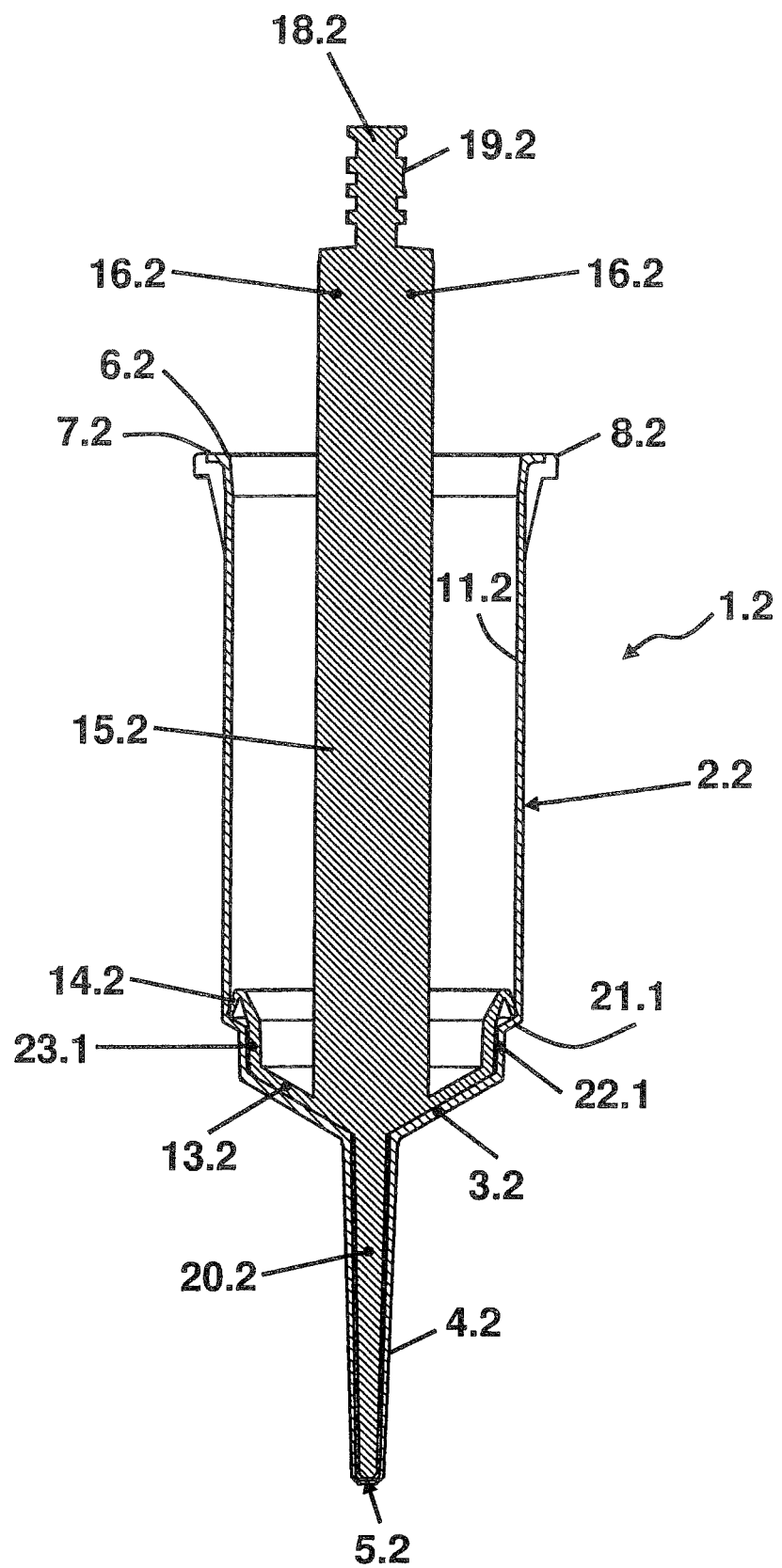
Figure 6:
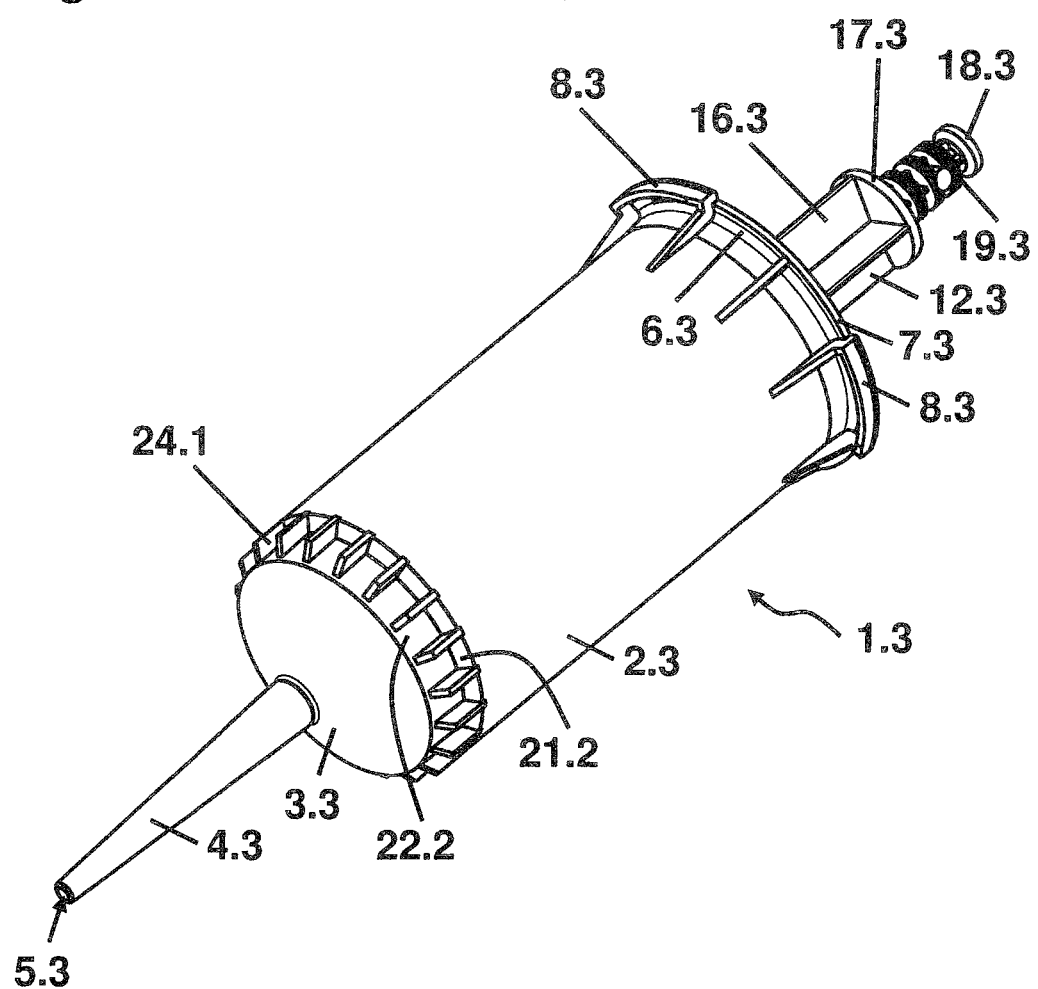
Figure 7:
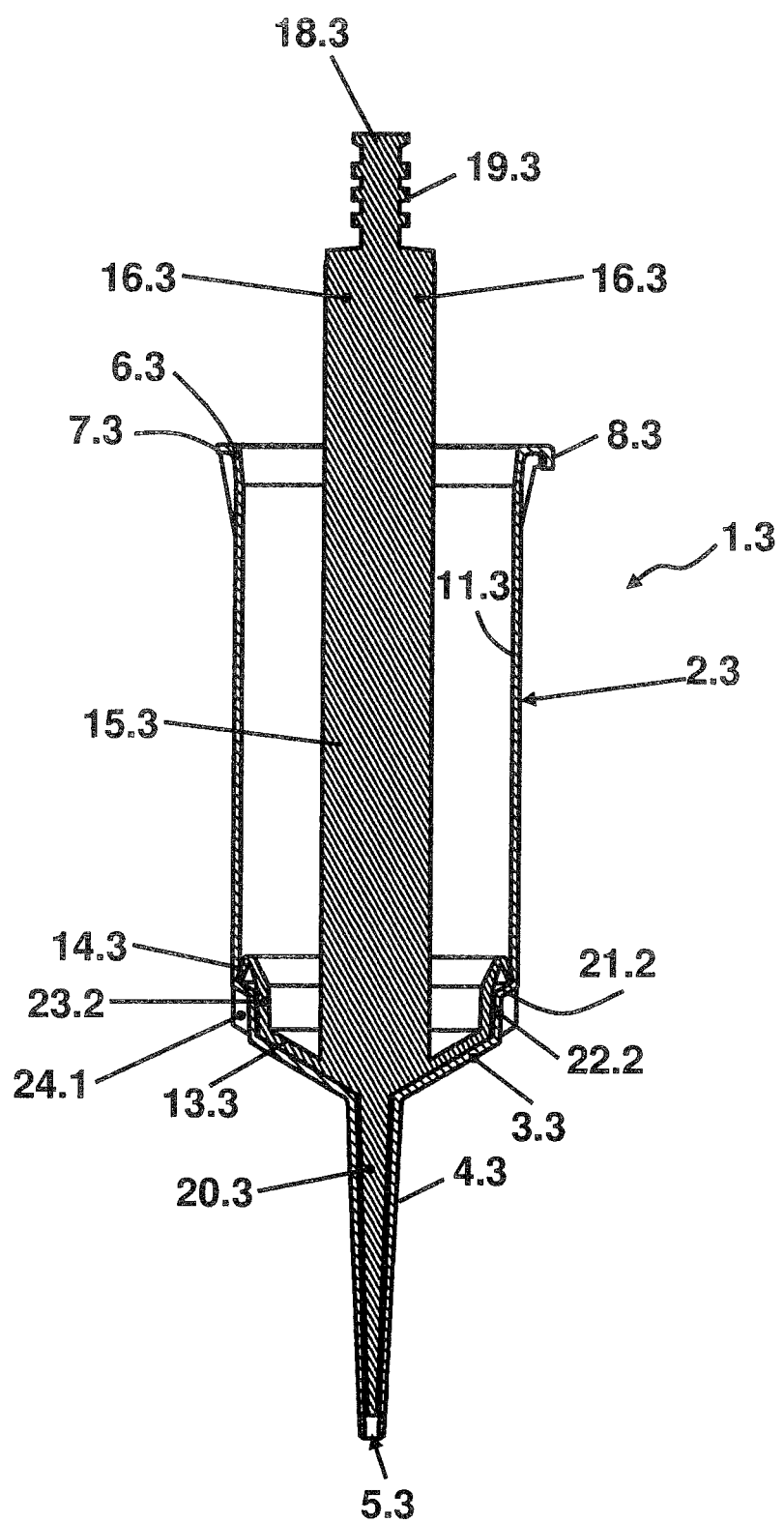
Figure 8:
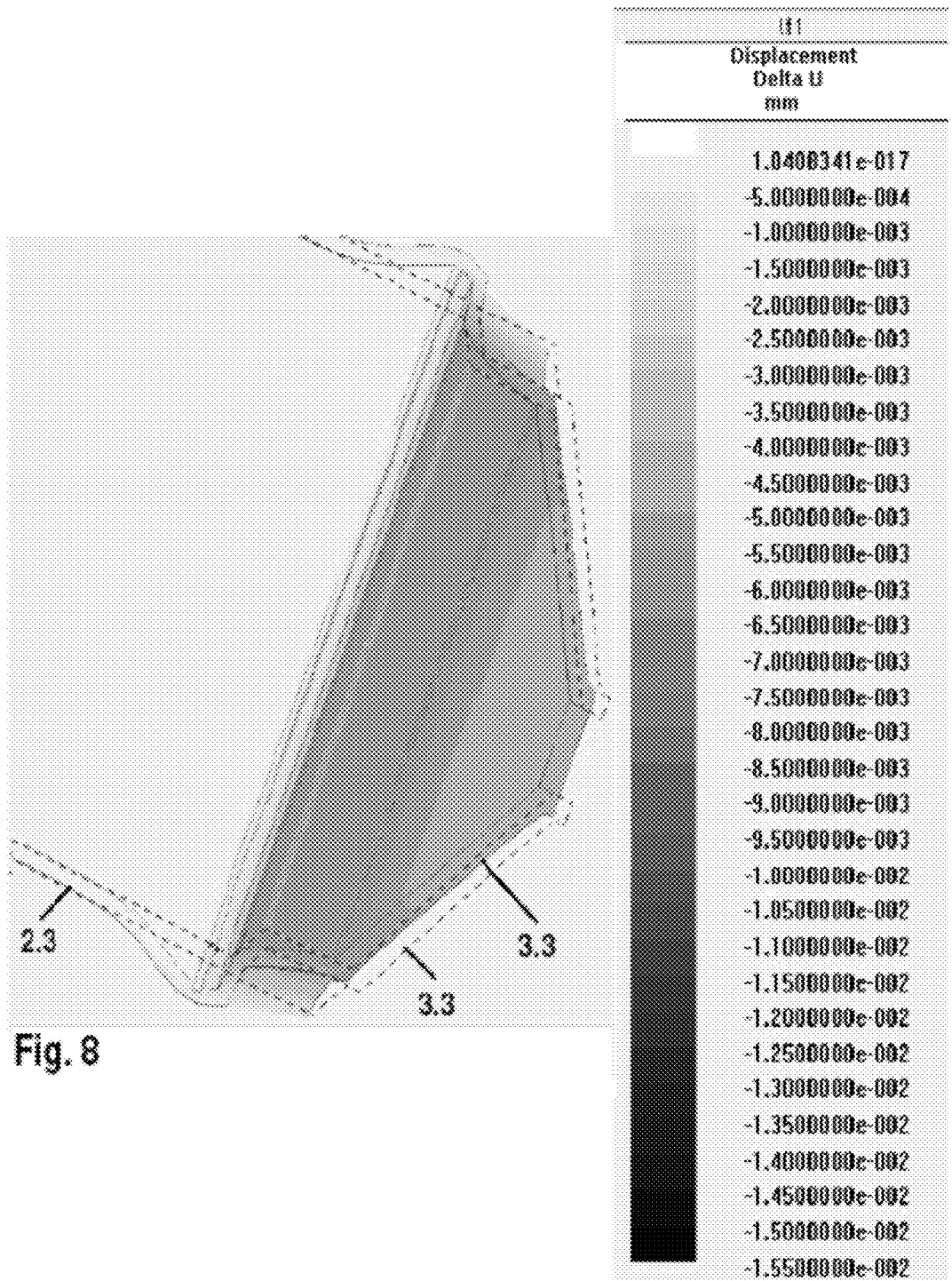
Figure 9:
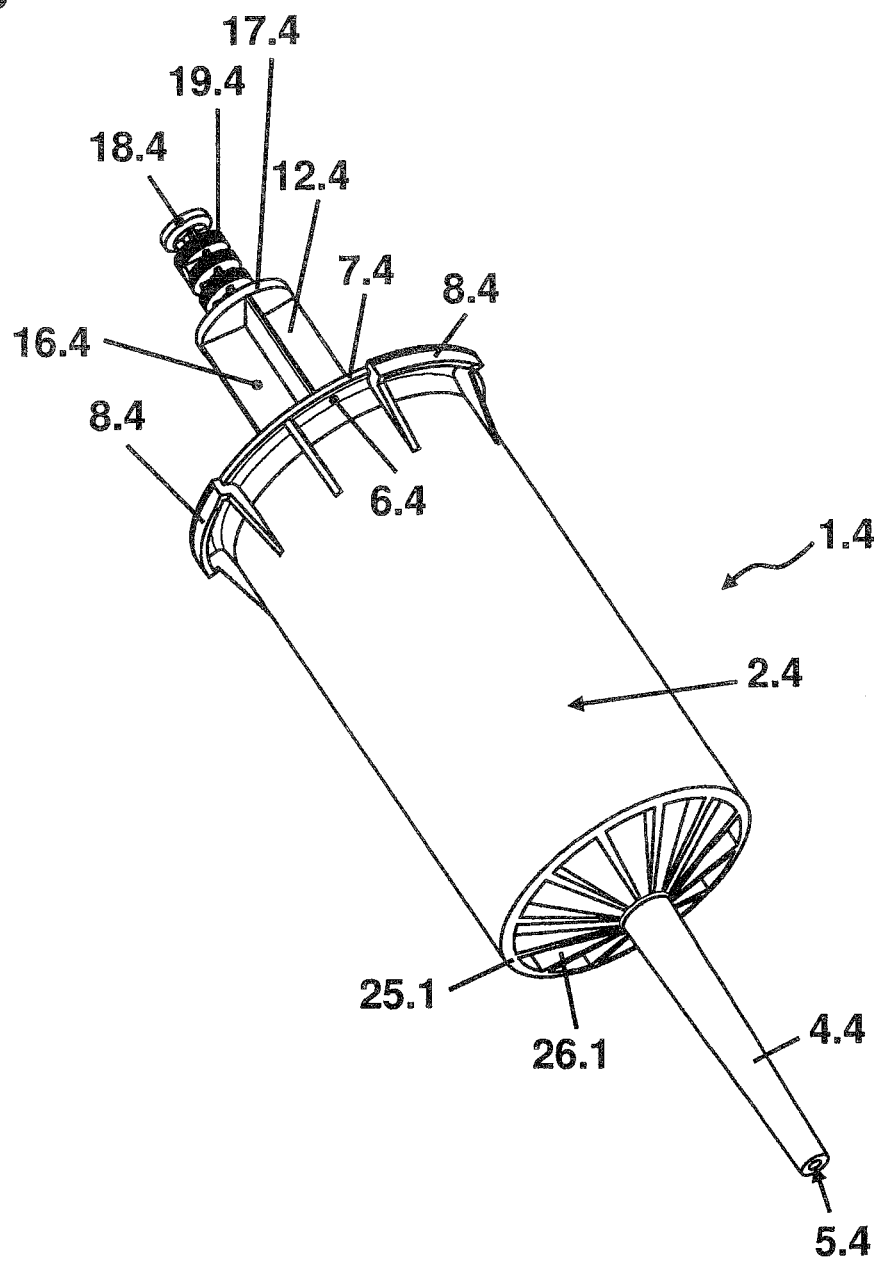
Figure 10:
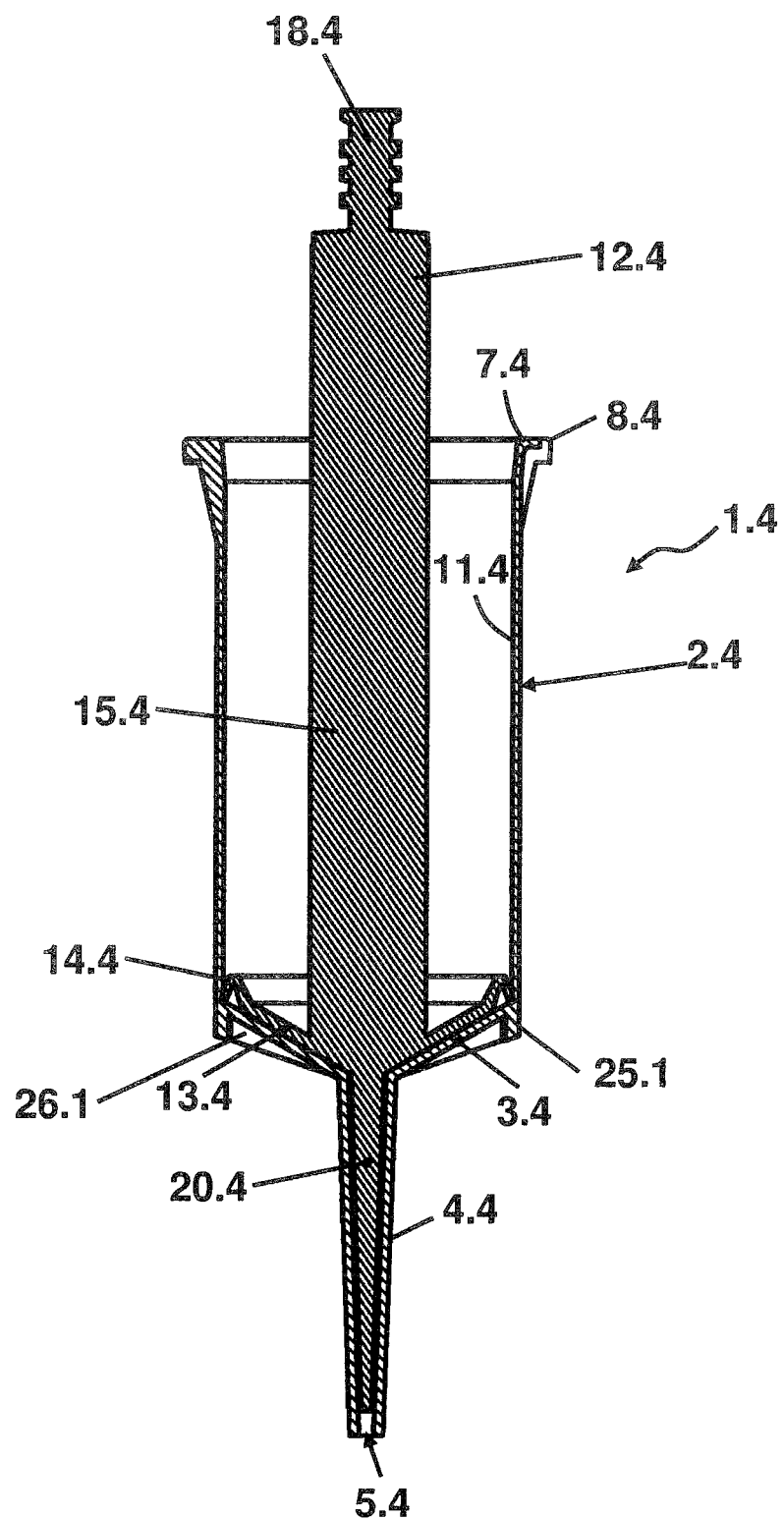
Figure 11:
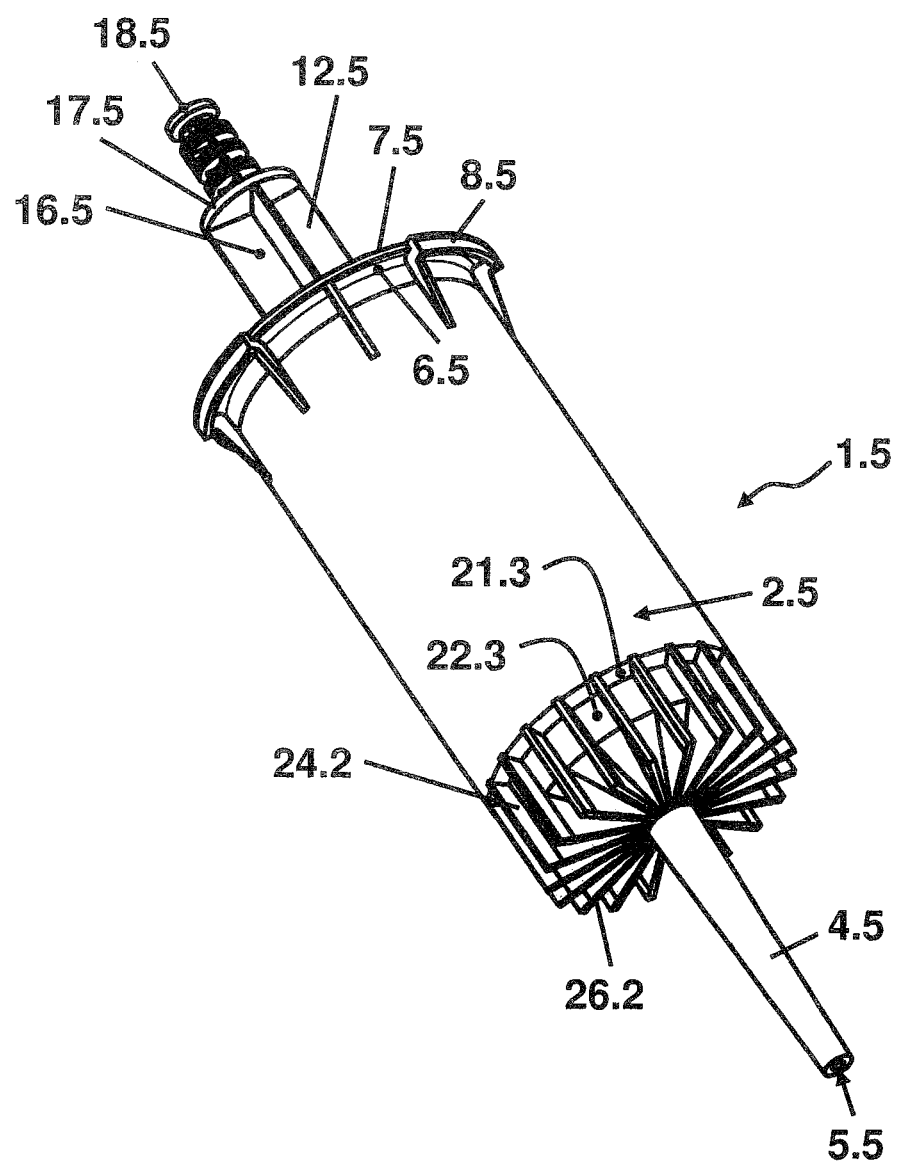
Figure 12:
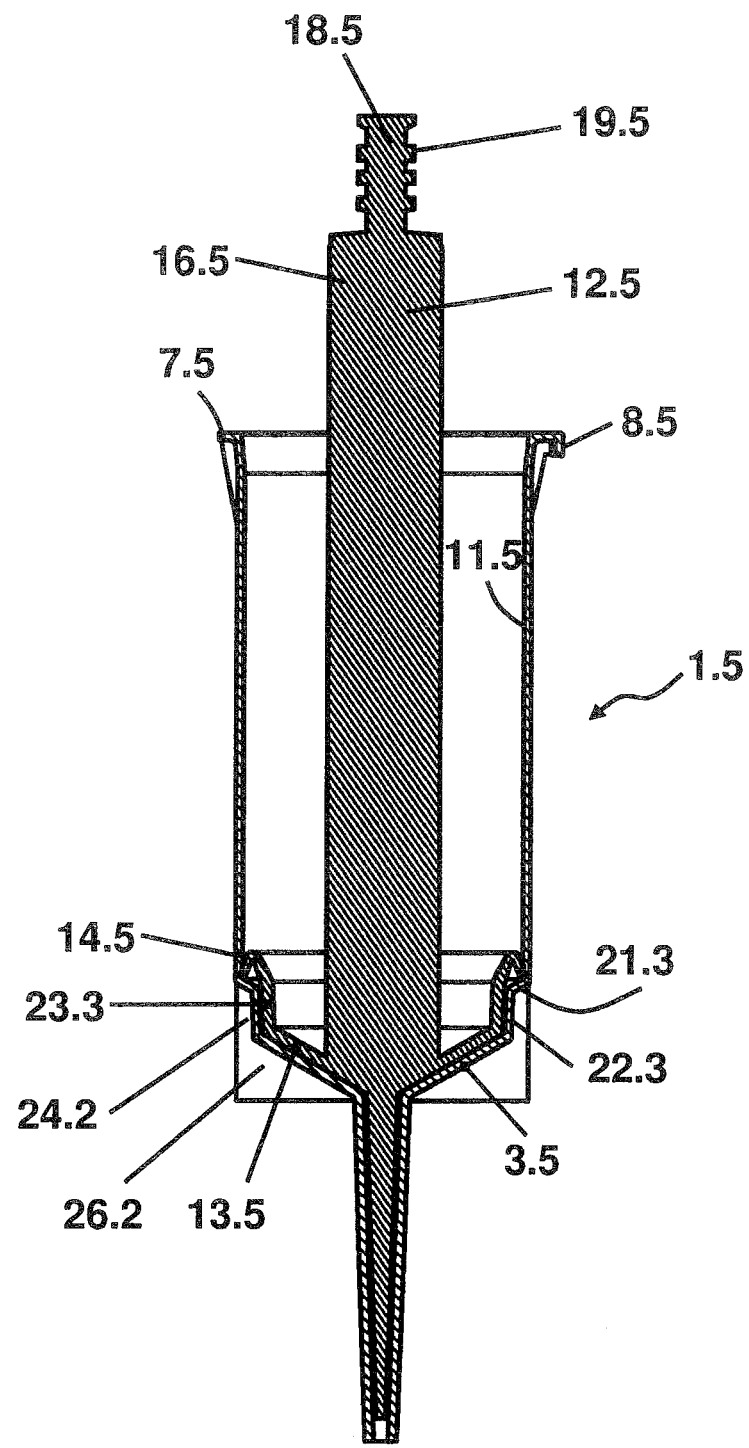

The invention is explained in greater detail using the attached drawings. The drawings show the following:

FIGS. 1 and 2 a conventional syringe in a perspective view diagonally from below and from the side (FIG. 1) and in a longitudinal cut (FIG. 2);

FIG. 3 a bottom section of the syringe cylinder of FIG. 1 in the case of an uninserted syringe plunger with dashed lines and in the case of a completely inserted syringe plunger with solid lines in 200-fold magnification, wherein the extent of the deformation of the floor is indicated by gray tones as per the legend;

FIGS. 4 and 5 a syringe according to the invention with an inner step of the syringe cylinder as stop for a sealing lip of the plunger in a perspective view diagonally from the bottom and from the side (FIG. 4) and in a longitudinal cut (FIG. 5);

FIGS. 6 and 7 a syringe according to the invention with an inner step of the syringe cylinder as stop for a sealing lip of the plunger with axially extending ribs on the perimeter of the syringe cylinder in a perspective view diagonally from the bottom and from the side (FIG. 6) and in a longitudinal cut (FIG. 7);

FIG. 8 a bottom section of the syringe cylinder of the syringe of FIG. 6 in the case of an uninserted syringe plunger with dashed lines and in the case of a completely inserted syringe plunger with solid lines, wherein the extent of the deformation of the floor is indicated by gray tones as per the legend;

FIGS. 9 and 10 a syringe according to the invention with radially extending ribs on the floor in a perspective view diagonally from below and from the side (FIG. 9) and in a longitudinal cut (FIG. 10);

FIGS. 11 and 12 a syringe according to the invention with inner step of the syringe cylinder as stop for a sealing lip of the syringe plunger, ribs extending axially on the perimeter of the syringe cylinder and ribs extending in continuation of the axially extending ribs radially on the floor of the syringe cylinder up to the outlet in a perspective view diagonally from below and from the side (FIG. 11) and in a longitudinal cut (FIG. 12).

In the following explanation, corresponding parts in different exemplary embodiments are provided with several reference numbers, which are separated from each other by a point, wherein the numbers preceding the point match and the numbers following the point indicate the respective exemplary embodiment. In summary, corresponding parts in different exemplary embodiments are also labelled alone with the matching numbers.

According to FIGS. 1 and 2, a conventional syringe 1.1 has a syringe cylinder 2.1, which on the bottom has a conical, downward tapering floor 3.1. At the deepest point of the floor 3.1, there is a downward protruding, downward conically tapering dosing tip 4.1. The dosing tip 4.1 has an outlet 5.1 for liquid.

The syringe cylinder 2.1 has an outward protruding flange 7.1 on the upper edge 6.1. Furthermore, three projections 8.1 protrude from the upper edge 6.1 even further outward than the flange 7.1. The projections 8.1 are evenly distributed over the perimeter of the syringe cylinder. The projections 8.1 form a bayonet joint with an adapter (not shown) for holding the syringe cylinder 2.1 in a dosing device (not shown).

The upper edge 6.1 surrounds an opening 9.1, which serves to insert a syringe plunger. Adjacent to the opening 9.1, the syringe cylinder has a short insertion slope 10.1 on the inside. A run area 11.1 for a syringe plunger, which extends up to floor 3.1, connects to it.

A syringe plunger 12.1 is inserted into the syringe cylinder 2.1. The syringe plunger 12.1 has a mainly conical plunger head 13.1 on the bottom. The plunger head 13.1 is provided on its outer perimeter with a sealing lip 14.1 with a V-shaped cross-section. The sealing lip 14.1 rests against the plunger run area 11.1 with its outer end circumferentially on this inside. The sealing lip 14.1 is open towards the floor 3.1 with its V cross-section.

On the top, the plunger head 13.1 carries a push rod 15.1, which is formed for the most part by four lamellar wing pieces 16.1, which are aligned with each other crosswise in a horizontal cross-section. On the top, a circular disk 17.1 sits on the wing pieces 16.1. A coupling piece 18.1, which has a series of circular-disk-like projections 19.1 arranged behind each other in the axial direction, is located on it. The coupling piece 18.1 is insertable into a plunger receiver of a dosing device (not shown) and is held therein by means of suitable holding means.

Furthermore, the plunger head 13.1 has a downward protruding, downward conically tapering displacement tip 20.1. The conicity of the plunger head 13.1 is adjusted for the conicity of the floor 3.1 and the conicity of the displacement tip 20.1 for the conicity of the dosing tip 4.1, without the plunger head sitting on the floor 3.1 and without the displacement tip 20.1 sitting on the dosing tip 4.1 when the syringe plunger 12.1 is completely pushed into the syringe cylinder 2.1.

The syringe cylinder 2.1 and the syringe plunger 12.1 are each injection molded as a single piece from a plastic, wherein e.g. the syringe cylinder 2.1 is injection molded from polypropylene and the syringe plunger 12.1 from polyethylene.

The applicant found out that during insertion of the syringe plunger 12.1 into the syringe cylinder 2.1 the syringe cylinder 2.1 expands radially over the sealing lip 14.1. When, during the last dosing step, the syringe plunger with the sealing lip 14.1 sits on the floor 3.1, this causes the syringe floor 3.1 to be deformed slightly inward into the syringe cylinder 2.1.

This is shown in FIG. 3. The deformation of the syringe cylinder shown in FIG. 3 is based on FEM calculations (calculations according to the Finite Element method). In these calculations, only the displacement of the floor with respect to its initial position in the axial direction was observed.

FIG. 3 shows the syringe cylinder 2.1 in dashed lines in the undeformed state when the syringe plunger 12.1 is not inserted. Furthermore, the syringe cylinder 2.1 in solid lines is shown in the situation in which the syringe plunger 12.1 is pushed in completely. It is easy to see that the syringe floor 3.1 curves into the inside of the syringe cylinder 2.1.

FIG. 3 shows the extent of the deformation of the floor 3.1 through different gray tones.

The syringe 1.2 according to the invention in FIGS. 4 and 5 differs from that described above in that the syringe cylinder 2.2 has a narrow shoulder 21.1 from the inner perimeter at a distance from floor 3.2. The shoulder 21.1 tapers conically downward. The plunger run area 11.2 of the syringe 1.2 is located above the shoulder 21.1. The syringe cylinder 2.2 has a cylindrical bottom end area 22.1 with a reduced diameter below the shoulder 21.1.

The syringe plunger 12.2 differs from the one described above 12.1 in that the conical plunger head 13.2 has a reduced diameter with a cylindrical section 23.1 protruding from the upper edge. The upper edge of the cylindrical section 23.1 is connected with the V-shaped sealing lip 14.2, the shape and dimensions of which match that of the sealing lip 14.1.

According to the design shown in FIGS. 6 and 7, the syringe 1.3 is unique in that the syringe cylinder 2.3 has axially extending ribs 24.1 on the outside below the bottom end area 22.2 with a reduced diameter. The axial ribs 24.1 extend from the outside of the inner step 21.2 almost to the floor 3.3. Their height is selected such that they do not project over the casing of the syringe cylinder 2.3. Approximately 10 to 30 axial ribs 24.1 are evenly distributed over the perimeter of the syringe cylinder 2.3.

When, in the case of syringes 1.2 or respectively 1.3, the syringe plunger 12.2 or respectively 12.3 is completely pushed into the syringe cylinder 2.2 or respectively 2.3, the sealing lip 14.2 or respectively 14.3 sits on the inner step 21.1 or respectively 21.2 and prevents further displacement of the syringe plunger 12.2 or respectively 12.3 to the floor 3.2 or respectively 3.3. The plunger head 13.2 or respectively 13.3 is distanced from the floor 3.2 or respectively 3.3 by a small gap and the displacement tip 20.2 or respectively 20.3 is distanced from the dosing tip 4.2 or respectively 4.3 by a small gap. The radial deformation caused by the sealing lip 14.2 or respectively 14.3 thus does not impact the floor 3.2 or respectively 3.3. In the case of the syringe 1.3, the axial ribs 24.1 also contribute to stabilize the shape of the syringe cylinder 2.3.

FIG. 8 shows the results of the further FEM calculation for the axial deformation of the syringe cylinder 2.3 of the syringe 1.3 from FIGS. 6 and 7. The undeformed syringe cylinder 2.3 is shown in turn in dashed lines. The syringe cylinder deformed by the syringe plunger 12.3 pushed forward up to the stop is shown in solid lines. The scale is the same as in FIG. 3. The deformations of the syringe floor 3.3 are extremely low. The gray tones show that the outer areas of the floor 3.3 are deformed somewhat stronger than the central areas.

FIGS. 9 and 10 show another syringe 1.4 according to the invention. This differs from the syringe 1.1 only in that the casing of the syringe cylinder 2.4 has an extension 25.1, which protrudes slightly over the floor 3.4. In the area of the extension 25.1, the wall thickness of the syringe cylinder 2.4 is greater than over the run area 11.4.

Furthermore, the syringe cylinder 2.4 has a plurality (e.g. 10 to 30) of radially extending ribs 26.1 on the bottom side of the floor. The radial ribs 26.1 are the highest adjacent to the extension 25.1. This is at least 3 mm. Starting from the outer perimeter, the height of the ribs 26.1 decreases up to the dosing tip 4.4. The radial ribs 26.1 are distributed evenly over the floor 3.4.

The radial ribs 26.1 effect a stabilization of the floor 3.4, which greatly reduces a deformation of the floor 3.4, when the sealing lip 14.4 sits on the inside of the floor 3.4. The extension 25.1 also contributes to the reduction in the deformation of the floor 3.4.

FIGS. 11 and 12 show another syringe 1.5 according to the invention, in which the syringe cylinder 2.5 has an inner step 21.3 and the syringe plunger 12.5 is designed like the syringe plunger 12.2. Moreover, the syringe cylinder 2.5 has axial ribs 24.2 on the outside (approx. 10 to 30) and floor 3.5 radial ribs 26.2 on the outside. The axial ribs 24.2 extend up to the floor 3.5 and there cross over into the radial ribs 26.2. On the outer perimeter of floor 3.5, the radial ribs are clearly higher than in syringe 1.4.

In the case of syringe 1.5, the deformation of the floor 3.5 is reduced and accompanying dosing errors are avoided through the displacement of the plunger seal 14.5 away from the floor 3.5 and through the stabilization of the floor 3.5 by axial ribs 24.2 and radial ribs 26.2.

The invention claimed is:

1. A syringe for use with a dosing device with a receiver for a syringe cylinder and an axially displaceable plunger receiver for a syringe plunger, the syringe comprising:
   a syringe cylinder, which has a floor with an outlet on the bottom, a cylindrical plunger run area on the inside and has means for being held in the receiver on the top,
   a syringe plunger, which has a circumferential plunger seal for sealing on the plunger run area on the perimeter, the plunger seal being a sealing lip, and
   a coupling piece for insertion into the plunger receiver on the top and
   a stop member between the syringe cylinder and the syringe plunger, which restricts the displacement of the syringe plunger toward the floor so that the syringe plunger with the plunger seal can only approach to a certain distance from the floor, said stop member being a circumferential inner step on the syringe cylinder, said inner step being arranged at a distance from the floor and restricts the displacement of the syringe plunger toward the floor in that the sealing lip rests on the inner step of the syringe cylinder such that the plunger seal of said plunger is above the floor and cannot reach said floor.

2. The syringe according to claim 1, in which the plunger below the plunger seal has a lower plunger section, which engages into a bottom end area of the syringe cylinder when the plunger seal approaches to a certain distance from the floor.

3. The syringe according to claim 1, in which the stop member has a circumferential inner step of the syringe cylinder, which is arranged at a distance from the floor and the displacement of the syringe plunger towards the floor is restricted, and in which the syringe cylinder below the inner step has a bottom end area with a reduced inner diameter.

4. The syringe according to claim 3, in which the syringe plunger below the plunger seal has a bottom plunger section with a reduced diameter, which engages into a bottom end area of the syringe cylinder when the plunger seal approaches to a certain distance from the floor.

5. The syringe according to claim 3, in which the syringe cylinder in the bottom end area with reduced inner diameter has axially extending ribs on the outside.

6. The syringe according to claim 1, in which the syringe cylinder has at least adjacent to the floor ribs extending axially to its perimeter on the outside.

7. The syringe according to claim 1, in which the floor has a cylindrical or downward tapering, conical shape.

8. The syringe according to claim 1, in which the outlet is arranged in a dosing tip protruding from the floor.

9. The syringe according to claim 1, in which the syringe plunger has a plunger head, which is connected with the coupling piece via a push rod.

10. The syringe according to claim 9, in which the push rod comprises several wing pieces extending in the longitudinal direction.

11. The syringe according to claim 1, in which the means for holding are a flange connected as one piece with the syringe cylinder and/or an adapter connected with the syringe cylinder with a flange for connecting the syringe cylinder with an adapter.

12. The syringe according to claim 1, in which the syringe cylinder and/or the syringe plunger are each produced as a single piece made of plastic.

13. A syringe for use with a dosing device with a receiver for a syringe cylinder and an axially displaceable plunger receiver for a syringe plunger, the syringe comprising:
a syringe cylinder, which has a floor with an outlet on the bottom, a cylindrical plunger run area on the inside and has means for being held in the receiver on the top,
a syringe plunger, which has a circumferential plunger seal for sealing on the plunger run area on the perimeter, the plunger seal being a sealing lip, and
a coupling piece for insertion into the plunger receiver on the top and
a stop member between the syringe cylinder and the syringe plunger, which restricts the displacement of the syringe plunger towards the floor so that the syringe plunger with the plunger seal can only approach to a certain distance from the floor, said stop member having a circumferential inner step of the syringe cylinder, which is arranged at a distance from the floor and restricts the displacement of the syringe plunger the floor, in that the sealing lip rests on the inner step of the syringe cylinder, in which the outlet is arranged in a dosing tip protruding from the floor, in which the syringe plunger has a displacement tip, which engages into the dosing tip when the syringe plunger is pushed as far as possible into the syringe cylinder.

14. A syringe for use with a dosing device with a receiver for a syringe cylinder and an axially displaceable plunger receiver for a syringe plunger, the syringe comprising:
a syringe cylinder, which has a floor with an outlet on the bottom in which the outlet is arranged in a dosing tip protruding from the floor, on the outside of the floor radially extending ribs with a rib height of at least 1 mm at least on the outer end,
a cylindrical plunger run area on the inside and has means for being held in the receiver on the top and
a syringe plunger, which has a circumferential plunger seal for sealing on the plunger run area on the perimeter and
a coupling piece for insertion into the plunger receiver on the top, in which the height of the radial ribs decreases from the outer perimeter up to the dosing tip.

15. The syringe according to claim 14, in which the radial ribs have at least on the outer end a height of at least 3 millimeters.

16. A syringe for use with a dosing device with a receiver for a syringe cylinder and an axially displaceable plunger receiver for a syringe plunger, the syringe comprising:
a syringe cylinder, which has a floor with an outlet on the bottom in which the outlet is arranged in a dosing tip protruding from the floor, on the outside of the floor radially extending ribs with a rib height of at least 1 mm at least on the outer end,
a cylindrical plunger run area on the inside and has means for being held in the receiver on the top and
a syringe plunger, which has a circumferential plunger seal for sealing on the plunger run area on the perimeter and
a coupling piece for insertion into the plunger receiver on the top, in which the syringe cylinder has at least adjacent to the floor ribs extending axially to its perimeter on the outside said ribs having a height which decreases up to said dosing tip.

* * * * *